(12) United States Patent
Abehasera

(10) Patent No.: US 10,918,184 B1
(45) Date of Patent: *Feb. 16, 2021

(54) SMART NOZZLE FOR HAIR DRYER

(71) Applicant: Bonalogic, LLC, Hallandale Beach, FL (US)

(72) Inventor: Benyamin Abehasera, Hallandale Beach, FL (US)

(73) Assignee: Tech 4 Hair, LLC, Hallandale Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/902,925

(22) Filed: Jun. 16, 2020

Related U.S. Application Data

(63) Continuation-in-part of application No. 16/803,526, filed on Feb. 27, 2020, now Pat. No. 10,722,017.

(51) Int. Cl.
*A45D 20/12* (2006.01)
*G01S 17/08* (2006.01)
*A61N 5/06* (2006.01)
*A45D 19/00* (2006.01)

(52) U.S. Cl.
CPC .......... *A45D 20/12* (2013.01); *A61N 5/0617* (2013.01); *G01S 17/08* (2013.01); *A45D 2019/0041* (2013.01)

(58) Field of Classification Search
CPC ....... G01S 15/04; G01S 7/523; G08B 13/191; A45D 20/12; A45D 1/00
See application file for complete search history.

(56) References Cited

U.S. PATENT DOCUMENTS

| | | | | |
|---|---|---|---|---|
| 3,612,069 A | * | 10/1971 | Waters | A45D 20/44 132/212 |
| 5,636,318 A | * | 6/1997 | Polaert | A45D 20/12 34/268 |
| 6,188,837 B1 | * | 2/2001 | Kwan | A45D 20/12 34/97 |
| 2008/0288007 A1 | * | 11/2008 | Malak | A61N 5/0617 607/2 |
| 2009/0234490 A1 | * | 9/2009 | Suprock | B23B 31/02 700/159 |
| 2010/0170104 A1 | * | 7/2010 | Shami | A45D 20/12 34/283 |
| 2014/0047727 A1 | * | 2/2014 | Torres | A45D 20/124 34/97 |
| 2018/0027940 A1 | * | 2/2018 | Goldman | H01M 2/1055 |

* cited by examiner

*Primary Examiner* — Omeed Alizada
(74) *Attorney, Agent, or Firm* — Berger Singerman LLP; Geoffrey Lottenberg

(57) ABSTRACT

A smart nozzle system for a hair dryer includes a proximity detection circuit, a temperature sensing circuit, a speed detection circuit, and a rotating nozzle vane, among other features. The nozzle includes a microcontroller and a wireless communication module to interface with an external computing device via an application. Also included is a camera, a timer, a fluid dispenser, and a therapeutic UV light. The power supply can be a dynamo powered by air flowing through the nozzle. The nozzle can be an add-on to existing hair dryers or can be integral with a hair dryer system.

18 Claims, 5 Drawing Sheets

SMART NOZZLE FOR HAIR DRYER

CROSS REFERENCE TO RELATED APPLICATIONS

This application is a continuation-in-part of U.S. patent application Ser. No. 16/803,526 filed Feb. 27, 2020, which application is incorporated herein by reference in its entirety.

It will be recognized that some or all of the figures are schematic representations for purposes of illustration and do not necessarily depict the actual relative sizes or locations of the elements shown. The figures are provided for the purpose of illustrating one or more embodiments of the invention with the explicit understanding that they will not be used to limit the scope or the meaning of the claims.

DETAILED DESCRIPTION OF THE INVENTION

In the following description, for the purposes of explanation, numerous specific details are set forth in order to provide a thorough understanding of the invention. It will be apparent, however, to one skilled in the art that the invention may be practiced without some of these specific details. Throughout this description, the embodiments and examples shown should be considered as exemplars, rather than as limitations on the invention. That is, the following description provides examples, and the accompanying drawings show various examples for the purposes of illustration. However, these examples should not be construed in a limiting sense as they are merely intended to provide examples of the invention rather than to provide an exhaustive list of all possible implementations of thereof.

Specific embodiments of the invention will now be further described by the following, non-limiting examples which will serve to illustrate various features. The examples are intended merely to facilitate an understanding of ways in which the invention may be practiced and to further enable those of skill in the art to practice the invention. Accordingly, the examples should not be construed as limiting the scope of the invention. In addition, reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable manner in one or more embodiments.

Figure 1:
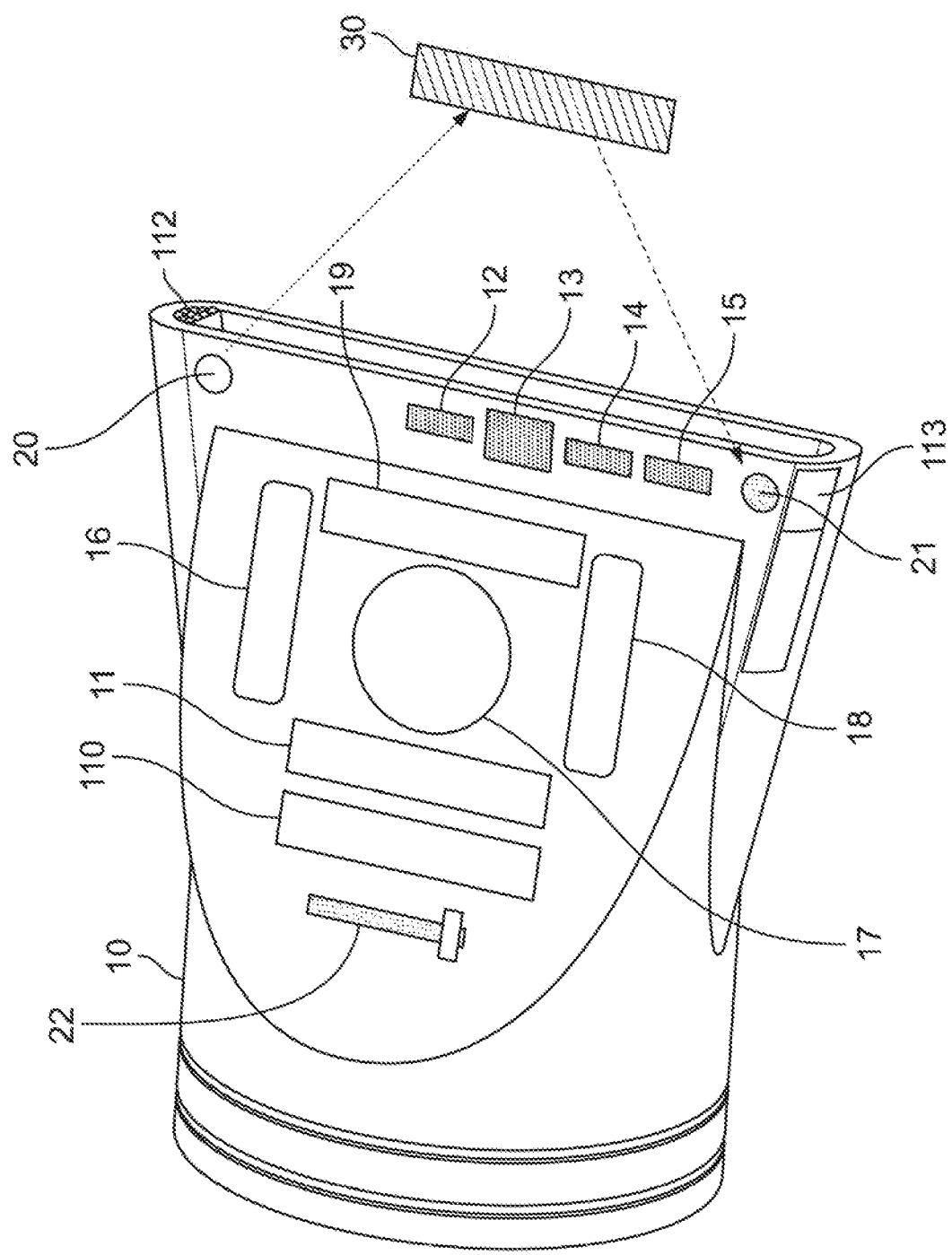
FIG. 1 is a schematic view of the hair dryer nozzle.
Figure 3:
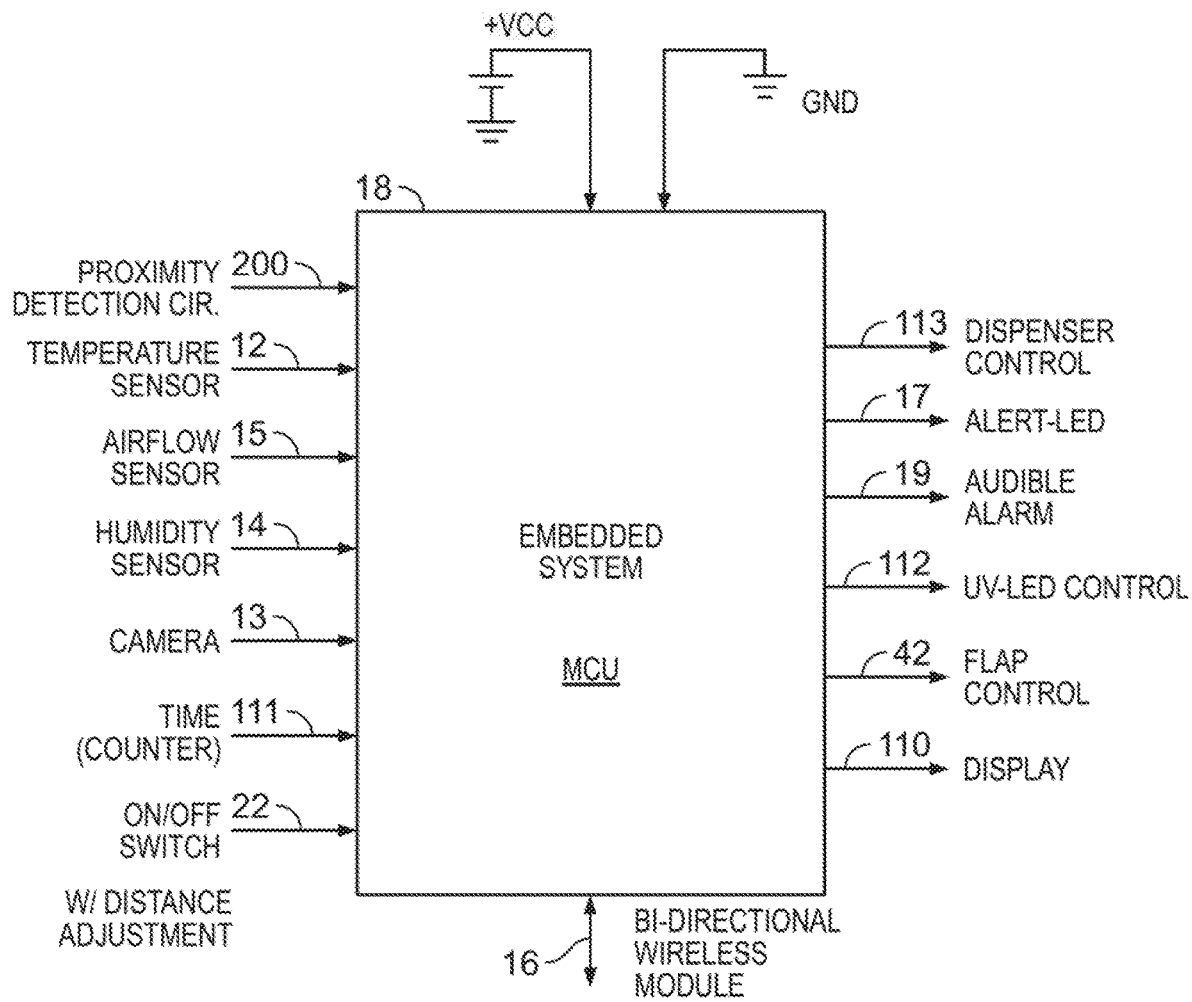
FIG. 3 is a system diagram of the hair dryer nozzle.

Referring to FIGS. 1 and 3 a hair dryer nozzle 10 is shown. The nozzle 10 can be configured as a removable "add-on" nozzle for an existing hair dryer or hair blow or it may be embedded and integrally formed with the hair dryer or hair blower itself. Note that as used herein the term "hair dryer" shall not be construed as limiting the function or purpose of the invention, rather it is used for convenience to describe the typical use of the product. Accordingly, the term "hair dryer" used herein is construed to also mean "hair blower" or other like tools known in the art. In the case the nozzle 10 is configured as an "add-on" device, it may form the shape and structure of typical hair dryer diffusers known in the art. The nozzle 10 includes several advanced "smart" features that add a variety of functionality to a typical hair dryer. The "smart" features of the nozzle 10 are primarily controlled by a microcontroller unit 18 which is data communication with a plurality of sensors including a temperature sensor 12, a humidity sensor 14, an and airflow sensor 15. The microcontroller unit 18 is also in data communication with a video camera 13, a wireless communications module 16, an alert LED (light-emitting diode) 17, and an audible alarm 19. In some embodiments the microcontroller unit 18 is in data communication with the hair dryer itself, including the heating element and blower motor thereof.

The nozzle 10 also includes a proximity detection circuit 200 (see FIG. 4) comprising an IR and/or photo-diode-based transmitter 20 and receiver 21. An adjustable on/off switch 22 turns the nozzle on and off and provides a means to adjust the range of the proximity detection circuit 200 as further described herein.

Figure 5:
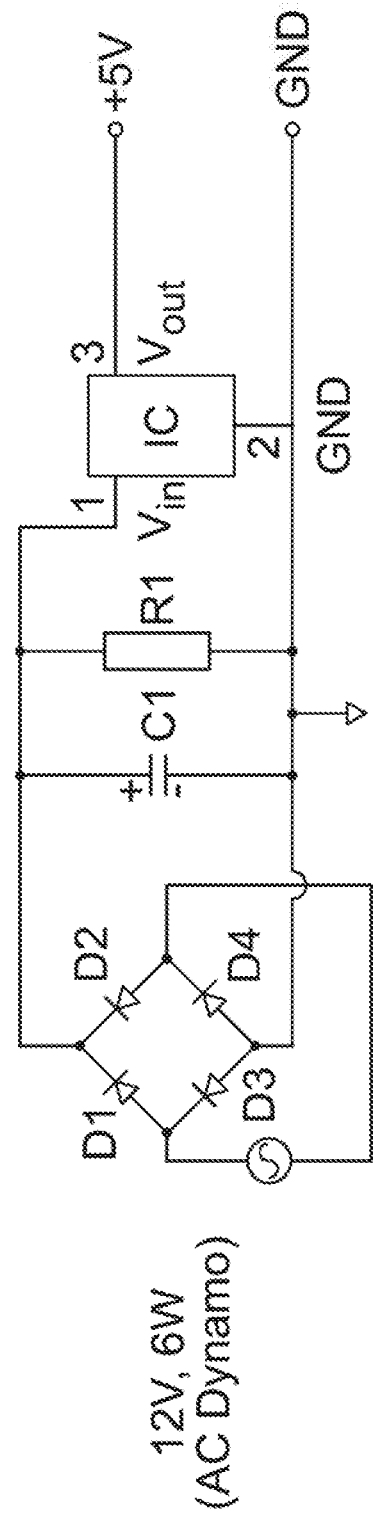
FIG. 5 is a circuit diagram of a dynamo-type power supply feature of the hair dryer nozzle.

In some embodiments, the nozzle is powered by a power supply 11 which may comprise a lithium ion battery or alkaline battery or other like power source. In some embodiments, the battery is rechargeable through a bus adapter on the nozzle 10, such as USB or the like. In some embodiments, the battery is wirelessly rechargeable. In other embodiments, the nozzle 10 can receive power from the mains power supply of the hair dryer or an external power source. In yet another embodiment, the nozzle 10 can receive power from an air-flow powered dynamo-type power supply, an exemplary circuit of which is shown in FIG. 5. The dynamo power supply circuit is placed downstream of the air-intake of the hair dryer and/or nozzle 10 such that passing air rotates the dynamo, which dynamo generates a voltage differential in responds to the changing magnetic field that results from rotation of the dynamo. In one example, the dynamo-type power supply is configured to generate 5V, which is sufficient to power typical microcontroller units 18 as described herein.

The temperature sensor 12 comprises a digital or analog sensor that detects the temperature of air flowing through the nozzle 10. In some embodiments, the temperature sensor 12 is configured to transmit temperature data to the microcontroller unit 18. The microcontroller unit 18 can react to temperature data by sounding an alert through audible alarm 19, and/or initiating a visible alert through LED 17, and/or sending a shut-off signal to the heating element or blower motor of the hair dryer if, for example, the air temperature exceeds or drops below a predetermined limit. In some embodiments, the microcontroller unit 18 continuously measures and samples temperature via the temperature sensor 12 while the nozzle and/or hair dryer is in use.

The humidity sensor 14 comprises a digital or analog sensor that detects the humidity (i.e. moisture) present in the air flowing through the nozzle 10 and/or at the vicinity of the distal end of the nozzle 10 (where air exits the nozzle). In some embodiments, the humidity sensor 14 is configured to transmit humidity data to the microcontroller unit 18. The microcontroller unit 18 can react to humidity data by sounding an alert through audible alarm 19, and/or initiating a visible alert through LED 17, and/or sending a shut-off signal to the heating element or blower motor of the hair dryer if, for example, humidity levels exceed or drop below a predetermined limit. In some embodiments, the microcontroller unit 18 continuously measures and samples humidity levels via the humidity sensor 14 while the nozzle and/or hair dryer is in use.

The airflow sensor 15 comprises a digital or analog sensor that detects rate of air flowing through the nozzle 10 and/or at the vicinity of the distal end of the nozzle 10 (where air exits the nozzle). In some embodiments, the airflow sensor 15 is configured to transmit airflow data to the microcontroller unit 18. The microcontroller unit 18 can react to airflow data by sounding an alert through audible alarm 19, and/or initiating a visible alert through LED 17, and/or sending a shut-off signal to blower motor of the hair dryer if, for example, the airflow rate exceeds or drops below a predetermined limit due to a blockage or other malfunction. In some embodiments, the microcontroller unit 18 continuously measures and samples airflow via the airflow sensor 15 while the nozzle and/or hair dryer is in use.

As discussed above, the alert LED (light-emitting diode) 17 and the audible alarm 19 are in data communication with the microcontroller unit 18 such that visual and/or audible alarms can be triggered by the microcontroller unit 18 in response to predetermine events or conditions as detected by the various sensors and other input/outputs of the nozzle 10. In some embodiments, the LED 17 can emit light of varying color and intensity. Likewise, the audible alarm 19 can emit sounds of varying types, lengths, tones, and volume levels.

In some embodiments, the nozzle 10 includes a timer 111 that is in data communication with the microcontroller unit 18. The timer 111 can function as a shut-off timer in communication with the on/off switch 22 in order to shut down the hair dryer after a predetermined amount of time has lapsed. In some embodiments, the timer 111 is in data communication with other system components such as the temperature sensor 12, humidity sensor 14, and/or air flow sensor 15 such that the microcontroller unit 18 can issue commands to relevant system components based on multiple inputs and sensor data.

In some embodiments, the nozzle 10 includes a proximity detection circuit 200 (see FIG. 4) that allows the nozzle 10 to detect comprising an IR transmitter 20 and receiver 21 and related electronic components including a photo-diode 23. In one example, the transmitter 20 emits outwardly an infrared signal that when intercepted by an object 30 (such as an individual's head, hair, or scalp) will deflect back to the receiver 21. The detection circuit 200 by way of the photodiode 23 generates a voltage level or voltage differential that can be used to calculate the distance between the transmitter and the object 30. The control and calculation portions of the proximity detection circuit 200 can be discrete from or embedded in the microcontroller unit 18. In some embodiments, the proximity detection circuit includes an operation amplifier and/or general purpose integrated circuit. Other distance measuring circuits may be employed such as laser-based systems. In some embodiments, the microcontroller unit 18 continuously measures and samples proximity to objects via the proximity detection circuit 200 while the nozzle and/or hair dryer is in use. This allows the nozzle 10 to detect and alert based on proximity to an object, such as someone's head, in order to enhance safety and effectivity.

An on/off switch 22 is provided which is in data communication with the microcontroller unit 18 to turn the nozzle 10 on and off. In some embodiments, the on/off switch 22 is configured as a sliding or rotating potentiometer such that the user can set the limits for a particular condition or combination of conditions such as distance, temperature, humidity, airflow, or time.

In some embodiments, the nozzle 10 includes a wireless communications module 16 such as a Bluetooth or WiFi chip. The communications module 16 is in data communication with the microcontroller unit 18 and is configured to wirelessly interface the nozzle 10 with external devices such as a computer, tablet, smartphone, smartwatch, or the like.

In some embodiments, the nozzle 10 includes a display 110 that is in data communication with the microcontroller unit 18 to display various information relating to the conditions and performance of the nozzle 10. For example, the display can show the temperature, humidity level, airflow rate, distance, battery level, wireless connectivity status and other status information, and combinations thereof. In some embodiments the display 110 is a touch panel display that also functions as an input device to control desired aspects of the nozzle 10.

The nozzle 10 may also include at its distal end or otherwise a camera 13, either video, still, or both, that is employed to allow one to remotely view the activity of the nozzle from a first-person perspective. Like other system components, the camera 13 is in data communication with the microcontroller unit 18. For example, through a mobile application discussed herein, a customer can view on his/her smartphone the work being done by a hairdresser or, alternatively, a user drying his/her own hair can get a more directly view at the back of his/her head in order to more effectively use the hair dryer.

Figure 2:
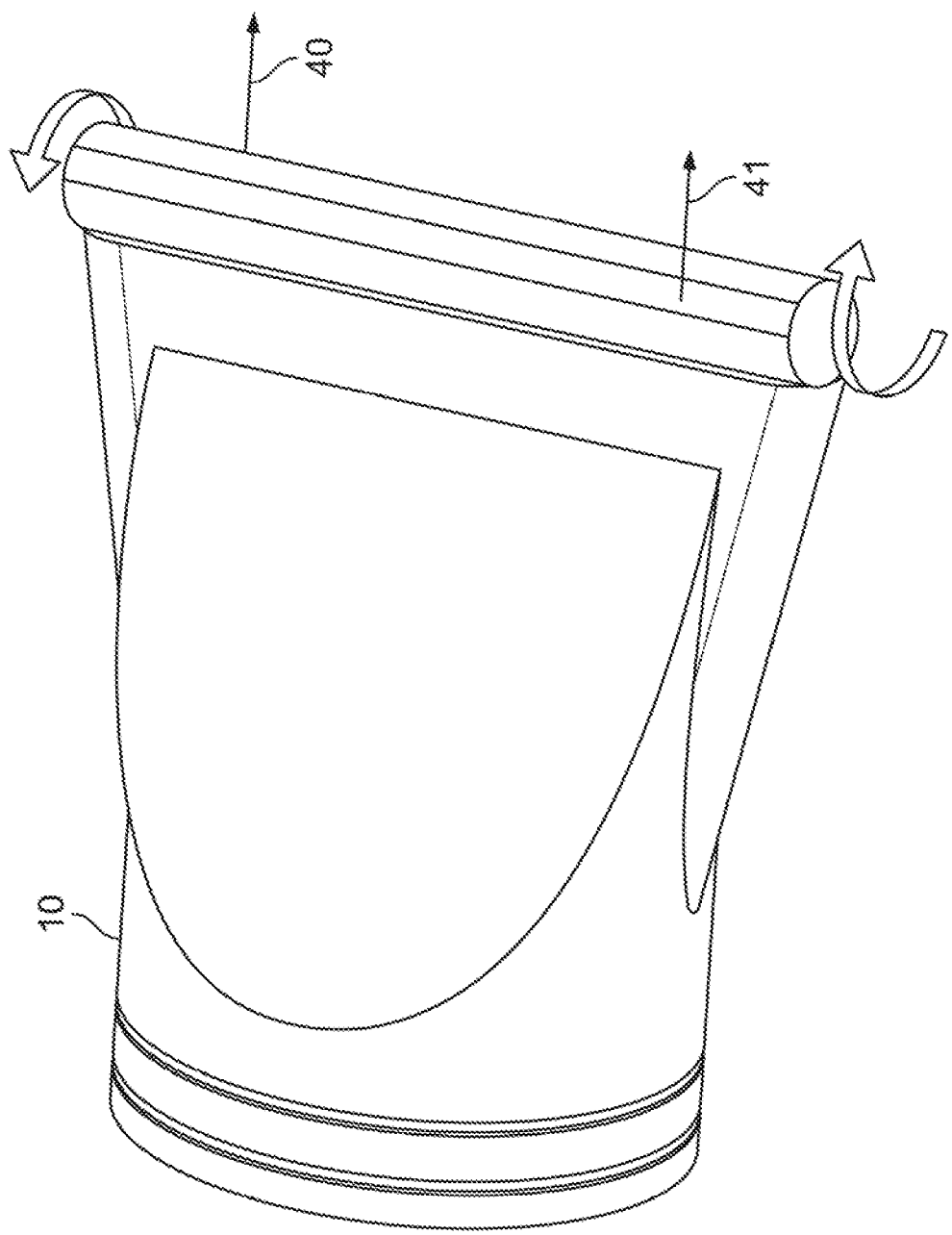
FIG. 2 is a schematic view of the hair dryer nozzle with a rotating airflow vane feature.
Figure 4:
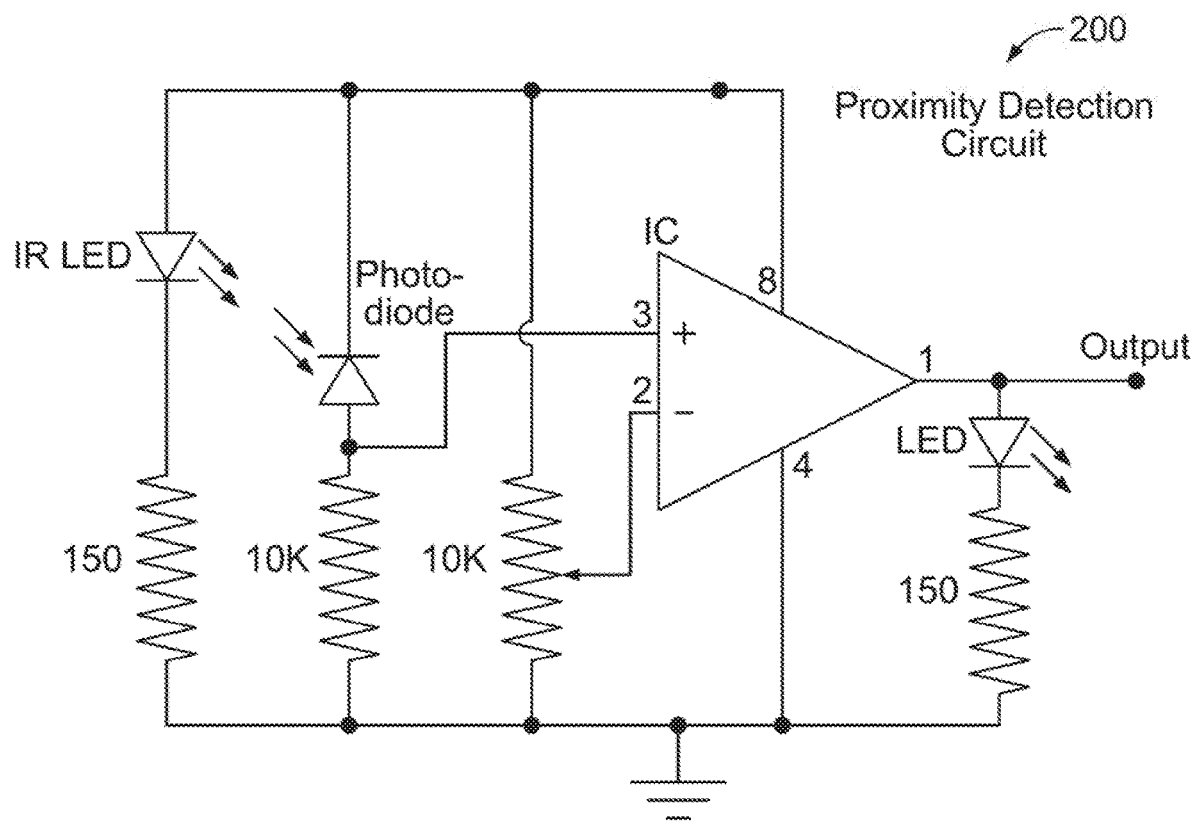
FIG. 4 is a circuit diagram of the proximity detection feature of the hair dryer nozzle.

With reference to FIG. 2, shown is another embodiment of the nozzle 10 a rotating airflow vane 40 that is disposed at the distal end of the nozzle 10. The airflow vane 40 includes an airflow output slot 41 that leaves open a portion of the surface area of the vane 40. The airflow vane 40 rotates either manually or by way of a small electric motor so that the user can position and direct the airflow out of the distal end of the nozzle 10. This allows the user to keep the position of nozzle 10 and/or hair dryer upright but direct the airflow in any desired direction relative to the distal end of the nozzle 10, making the nozzle 10 and/or hair dryer much more ergonomic to operate. For example, airflow can be directed upward although the nozzle is positioned relatively parallel to the floor. In addition to direction control, the vane 40 can also be used to control the amount and speed of air exiting the nozzle 10. With reference to FIG. 4, in some embodiments the vane 40 is controlled by vane controller 42 which allows for electronic actuation of the vane 40 by way of an electric motor.

In some embodiments, the nozzle 10 includes a UV-LED light system 112 which, in some embodiments, is located at the distal end of the nozzle 10. The light system 112 is configured to general UV light outwardly from the working end of the nozzle 10 toward the target in order to sanitize and otherwise provide therapeutic treatment for the target's scalp and hair. In some embodiments, the UV-LED light system 112 is adjustable to control the pulse-width modulation and the frequency of UV light. FIG. 5 is an exemplary circuit diagram of one embodiment of the UV-LED light system 112.

In some embodiments, the nozzle 10 includes a liquid, fluid, or vapor dispenser 113 that is configured as an electronic sprayer, a manual sprayer, or an electronic steam generator. The dispenser 113 can be configured either as an "open" system meaning it can be connected to an external fluid supply through a port or aperture on the nozzle 10 or it may be configured as a "closed" system wherein a fillable capsule is provided in a cavity in the nozzle 10. In an electronic sprayer embodiment, the nozzle 10 includes a button or actuator that is configured either for momentary use, i.e. on-demand spraying, or automatic operation wherein fluid is sprayed at a predetermined time interval or based on a predetermined temperature, humidity, or airflow condition. In a manual sprayer embodiment, the nozzle 10 includes a mechanical trigger that actuates an air-siphoned, positive displacement pump-action sprayer of conventional type. In an electronic steam generator embodiment, a small electronic steam generator (such a s filament-based heater) is disposed inside the nozzle 10 and/or hair dryer which accepts a feed of fluid from either an external source or an internal tank and heats that liquid into a steam which can be expelled from the dispenser 113 on demand or automatically but a button or actuator on the nozzle 10 or hair dryer. In some embodiments, the working fluid for the dispenser 113 is water.

With reference to FIG. 3, shown is a schematic of an embodiment of electronics of the nozzle 10 configured as an embedded system wherein all or most of the relevant system components are in electronically connected to the microcontroller 18 so that the microcontroller 18 can manage and control various system activities. In some embodiments, the embedded system provides and controls power distribution from the power supply 11 to the one or more of the system components. Yet still, in some embodiments the microcontroller 18 contains logic that allows the nozzle 10 to communicate to one or more external computing devices through the wireless module 16, such as for example to a computer, smartphone, smartwatch, tablet or the like. This enables to the user to control the features of the nozzle 10 through an application ("app") executing on the external device. In some embodiments, the external computing device establishes a two-way communications link with microcontroller 18 via wireless module 16 to enable and execute various features and functionality, including monitoring of system conditions, video/camera remote review, and other remote control functionality. In other embodiments, an external device can establish a communications link with the microcontroller 18 through a hardwired connection such as USB or the like, via a bus connector on the nozzle 10. In some embodiments a single bus connector on the nozzle 10 enables both power and communication links.

As noted above, the external computing device can include any smart phone, tablet computer, laptop computer, or other computing or mobile device capable of reading, and/or recording data about systems, devices, locations, and/or equipment, etc. In some embodiments, either or both of the microcontroller 18 (as an embedded system) or the external computing device (hereinafter each a "computing system") includes a processing system, storage system, software, communication interface, and user interface. Processing system loads and executes software from storage system, including software module. When executed by computing system, software module directs processing system to receive data, images, devices, locations, and/or equipment, etc. Such data could include any of the information described above, including but not limited to the functionality described throughout this disclosure. Although computing system includes one software module in the present example, it should be understood that one or more modules could provide the same operation. Similarly, the computing systems may be distributed using other computing systems and software.

Additionally, computing system includes communication interface (such as wireless module 16, in the case of the microcontroller 18) that can be further configured to transmit the collected data to computing system using communication network. Communication network could include the Internet, cellular network, satellite network, RF communication, blue-tooth type communication, near field, or any other form of communication network capable of facilitating communication between systems. In some examples, communication interface can further include a global positioning system to determine the location of computing system.

Processing system can comprise a microprocessor and other circuitry that retrieves and executes software from storage system. Processing system can be implemented within a single processing device but can also be distributed across multiple processing devices or sub-systems that cooperate in executing program instructions. Examples of processing system include general purpose central processing units, application specific processors, and logic devices, as well as any other type of processing device, combinations of processing devices, or variations thereof. Storage system can comprise any storage media readable by processing system, and capable of storing software. Storage system can include volatile and nonvolatile, removable and non-removable media implemented in any method or technology for storage of information, such as computer readable instructions, data structures, program modules, or other data. Storage system can be implemented as a single storage device but may also be implemented across multiple storage devices or sub-systems. Storage system can comprise additional elements, such as a controller, capable of communicating with processing system.

Examples of storage media include random access memory, read only memory, magnetic disks, optical disks, flash memory, virtual memory, and non-virtual memory, magnetic cassettes, magnetic tape, magnetic disk storage or other magnetic storage devices, or any other medium which can be used to store the desired information and that may be accessed by an instruction execution system, as well as any combination or variation thereof, or any other type of storage media. In some implementations, the storage media can be a non-transitory storage media. In some implementations, at least a portion of the storage media may be transitory. It should be understood that in no case is the storage media a propagated signal. Although one software module is shown, the software may be distributed across many devices, storage media, etc.

User interface can include a mouse, a keyboard, a camera, image capture, a voice input device, a touch input device for receiving a gesture from a user, a motion input device for detecting non-touch gestures and other motions by a user, and other comparable input devices and associated processing elements capable of receiving user input from a user. These input devices can be used for defining and receiving data about the location, maps, systems, devices, locations, and/or equipment, etc. Output devices such as a graphical display, speakers, printer, haptic devices, and other types of output devices may also be included in user interface.

It is to be noticed that the term "comprising," used in the claims, should not be interpreted as being limitative to the means listed thereafter. Thus, the scope of the expression "a device comprising means A and B" should not be limited to devices consisting only of components A and B. It means that with respect to the present invention, the only relevant components of the device are A and B. Put differently, the terms "including", "comprising" and variations thereof mean "including but not limited to", unless expressly specified otherwise.

Similarly, it is to be noticed that the term "coupled", also used in the claims, should not be interpreted as being limitative to direct connections only. Thus, the scope of the expression "a device A coupled to a device B" should not be limited to devices or systems wherein an output of device A is directly connected to an input of device B. It means that there exists a path between an output of A and an input of B which may be a path including other devices or means.

The enumerated listing of items does not imply that any or all of the items are mutually exclusive, unless expressly specified otherwise. The terms "a", "an" and "the" mean "one or more", unless expressly specified otherwise.

Elements of the invention that are in communication with each other need not be in continuous communication with each other, unless expressly specified otherwise. In addition, elements of the invention that are in communication with each other may communicate directly or indirectly through one or more other elements or other intermediaries.

One skilled in the art will appreciate that the present invention can be practiced by other than the above-described embodiments, which are presented in this description for purposes of illustration and not of limitation. The specification and drawings are not intended to limit the exclusionary scope of this patent document. It is noted that various equivalents for the particular embodiments discussed in this description may practice the invention as well. That is, while the present invention has been described in conjunction with specific embodiments, it is evident that any alternatives, modifications, permutations and variations will become apparent to those of ordinary skill in the art in light of the foregoing description. Accordingly, it is intended that the present invention embrace all such alternatives, modifications and variations as fall within the scope of the appended claims. The fact that a product, process or method exhibits differences from one or more of the above-described exemplary embodiments does not mean that the product or process is outside the scope (literal scope and/or other legally-recognized scope) of the following claims.

What is claimed is:

1. A nozzle for a hair dryer, comprising:
   a power supply, a microcontroller, a proximity detection circuit, and an alarm;
   wherein the power supply powers the microcontroller and the proximity detection circuit;
   wherein the microcontroller controls the proximity detection circuit;
   wherein the proximity detection circuit comprises an IR transmitter, an IR receiver, and at least one photo-diode;
   wherein the transmitter emits outwardly an infrared signal that when intercepted by the object deflects back to the receiver;
   wherein a photo-diode generates a voltage differential in response to the infrared signal, which voltage differential corresponds to a distance between the nozzle and the object;
   wherein the predetermined distance is adjustable; and
   wherein the proximity detection circuit triggers the alarm when an object is detected at or within a predetermined distance from the nozzle.

2. The nozzle of claim 1, wherein the power supply comprises a dynamo circuit which generates electricity in response to air passing through the nozzle.

3. The nozzle of claim 1, including a display.

4. The nozzle of claim 1, including a camera.

5. The nozzle of claim 1, including a wireless module configured to send and receive data to and from an external computing device.

6. The nozzle of claim 1, including an airflow sensor in data communication with the microcontroller configured to trigger the alarm when airflow drops or exceeds a predetermined level.

7. The nozzle of claim 1, including a temperature sensor in data communication with the microcontroller configured to trigger the alarm when air temperature drops or exceeds a predetermined level.

8. The nozzle of claim 1, including a humidity sensor in data communication with the microcontroller configured to trigger the alarm when air humidity drops or exceeds a predetermined level.

9. The nozzle of claim 1, including a timer circuit in data communication with the microcontroller.

10. The nozzle of claim 1, including a therapeutic ultraviolet light emitting diode (UV-LED) disposed at the distal end thereof.

11. The nozzle of claim 2, including a rotating vane disposed at the distal end thereof, the vane configured to direct airflow exiting the distal end of the nozzle.

12. The nozzle of claim 11, wherein the rotating vane is controlled by an electric motor, the electric motor in data communication with the microcontroller.

13. The nozzle of claim 12, including a fluid dispenser.

14. The nozzle of claim 13, wherein the fluid dispenser comprises an electronic steam generator.

15. A nozzle for a hair dryer, comprising:
   a microcontroller, a power supply, and the following system components: a proximity detection circuit, a display, a wireless module, and an alarm;
   wherein the power supply powers the microcontroller and the system components;
   wherein the microcontroller is in data communication with the system components;
   wherein the proximity detection circuit comprises an IR transmitter, an IR receiver, and at least one photo-diode;
   wherein the transmitter emits outwardly an infrared signal that when intercepted by the object deflects back to the receiver;
   wherein a photo-diode generates a voltage differential in response to the infrared signal, which voltage differential corresponds to a distance between the nozzle and the object;
   wherein the predetermined distance is adjustable; and
   wherein the proximity detection circuit is configured to trigger the alarm when an object is detected at or within a predetermined distance from the nozzle.

16. The nozzle of claim 15, wherein the power supply comprises a dynamo circuit which generates electricity in response to air passing through the nozzle.

17. The nozzle of claim 15, including a therapeutic ultraviolet light emitting diode (UV-LED) disposed at the distal end thereof.

18. The nozzle of claim 15, including a fluid dispenser.

* * * * *